(12) United States Patent
Dahlquist

(10) Patent No.: US 8,615,815 B2
(45) Date of Patent: Dec. 31, 2013

(54) UNDERGARMENT FOR HERNIA RELIEF AND OTHER PURPOSES

(75) Inventor: Daryl Dahlquist, Kent, WA (US)

(73) Assignee: Daryl Lervy Dahlquist, Kent, WA (US)

( * ) Notice: Subject to any disclaimer, the term of this patent is extended or adjusted under 35 U.S.C. 154(b) by 0 days.

(21) Appl. No.: 13/506,184

(22) Filed: Apr. 2, 2012

(65) Prior Publication Data

US 2012/0253256 A1 Oct. 4, 2012

Related U.S. Application Data

(63) Continuation of application No. 12/322,648, filed on Feb. 5, 2009, now abandoned, which is a continuation of application No. 11/147,693, filed on Jun. 8, 2005, now abandoned.

(60) Provisional application No. 60/580,115, filed on Jun. 16, 2004.

(51) Int. Cl.
A41B 9/02 (2006.01)

(52) U.S. Cl.
USPC ..................................... 2/400; 2/403; 602/67

(58) Field of Classification Search
USPC ............. 2/400–406, 236; 604/385.09; 602/67
See application file for complete search history.

(56) References Cited

U.S. PATENT DOCUMENTS

| | | | | |
|---|---|---|---|---|
| 792,424 A * | 6/1905 | King | ............................. | 128/96.1 |
| 898,258 A * | 9/1908 | Peters | ............................. | 602/69 |
| 1,263,576 A * | 4/1918 | Linneros | ........................ | 602/67 |
| 1,339,070 A * | 5/1920 | Sanders | ........................... | 602/67 |
| 1,992,351 A * | 2/1935 | Burnell | ............................ | 602/67 |
| 2,593,262 A * | 4/1952 | Calabrese | ...................... | 128/96.1 |
| 2,601,602 A * | 6/1952 | Firsching, Sr. | .................. | 602/67 |
| 2,684,637 A | 7/1954 | Lerman | | |
| 2,684,673 A * | 7/1954 | Lerman | ........................... | 602/79 |
| 2,742,647 A * | 4/1956 | Khalil | ............................... | 2/236 |
| 2,842,129 A * | 7/1958 | Ernstorff | ...................... | 604/396 |
| 2,872,685 A * | 2/1959 | Denbo | .............................. | 2/403 |
| 3,037,503 A * | 6/1962 | Ravaschieri | .................... | 602/69 |
| 3,517,666 A * | 6/1970 | Atlee | ............................... | 602/68 |
| 3,621,846 A * | 11/1971 | Lehman | ............................. | 2/67 |
| 4,035,844 A * | 7/1977 | Atack et al. | ....................... | 2/466 |
| 4,059,103 A * | 11/1977 | Glaser | ........................... | 128/96.1 |
| 4,345,337 A * | 8/1982 | Chung | .............................. | 2/405 |
| 4,377,008 A * | 3/1983 | Jung | ................................. | 2/403 |
| 4,416,272 A * | 11/1983 | Nelkin | ........................... | 128/95.1 |
| 4,660,551 A * | 4/1987 | Nishimura | ...................... | 600/41 |
| 4,669,130 A * | 6/1987 | Brown | .............................. | 2/227 |
| 4,697,592 A * | 10/1987 | Maddux et al. | ............... | 450/155 |
| 4,759,355 A * | 7/1988 | Thrower | .......................... | 602/67 |
| 4,870,958 A * | 10/1989 | Webster | ........................... | 602/67 |
| 5,029,345 A * | 7/1991 | Angheluta et al. | ................. | 2/403 |
| 5,134,726 A * | 8/1992 | Ross | ................................. | 2/465 |

(Continued)

Primary Examiner — Richale Quinn

(57) ABSTRACT

A brief style elastic undergarment designed for the particular needs of a portly person having an enlarged abdomen. The undergarment is constructed of elastic spandex material and has a high cut back and a low cut front so the waistband traverses the torso passing across the small of the back thence under the abdomen. The undergarment further comprising an auxiliary elastic waistband specifically intended to hold abdominal hernias in, and an attached supporting undershirt. Thus the elastic in the briefs and the auxiliary band press small hernias back into the abdominal cavity. For use by males, there is a hole through which the penis and scrotum project to avoid being compressed and allowing a snug, pressure fit across the front. The garment may be used as sleepwear and athletic wear.

3 Claims, 3 Drawing Sheets

(56) References Cited

U.S. PATENT DOCUMENTS

| | | | |
|---|---|---|---|
| 5,283,912 A * | 2/1994 | Chung | 2/403 |
| 5,618,279 A * | 4/1997 | Pudlo | 604/385.09 |
| 5,647,065 A * | 7/1997 | Richerson | 2/403 |
| 5,651,144 A * | 7/1997 | Li | 2/403 |
| 5,819,323 A * | 10/1998 | Edenfield | 2/466 |
| 5,870,779 A * | 2/1999 | Heron | 2/403 |
| 5,875,495 A * | 3/1999 | Thrower | 2/403 |
| 6,038,703 A * | 3/2000 | Chung | 2/403 |
| 6,047,408 A * | 4/2000 | Brill, Jr. | 2/403 |
| 6,243,880 B1 * | 6/2001 | Lyden | 2/228 |
| 6,353,940 B1 * | 3/2002 | Lyden | 2/403 |
| 6,622,719 B1 * | 9/2003 | Slautterback et al. | 128/98.1 |
| D482,512 S * | 11/2003 | Slautterback et al. | D2/712 |
| 6,868,850 B2 * | 3/2005 | Takenaga | 128/96.1 |
| 7,024,703 B1 * | 4/2006 | Della Ratta | 2/403 |
| 7,578,009 B1 * | 8/2009 | Boston | 2/405 |
| 7,788,739 B1 * | 9/2010 | Della Ratta | 2/403 |

* cited by examiner

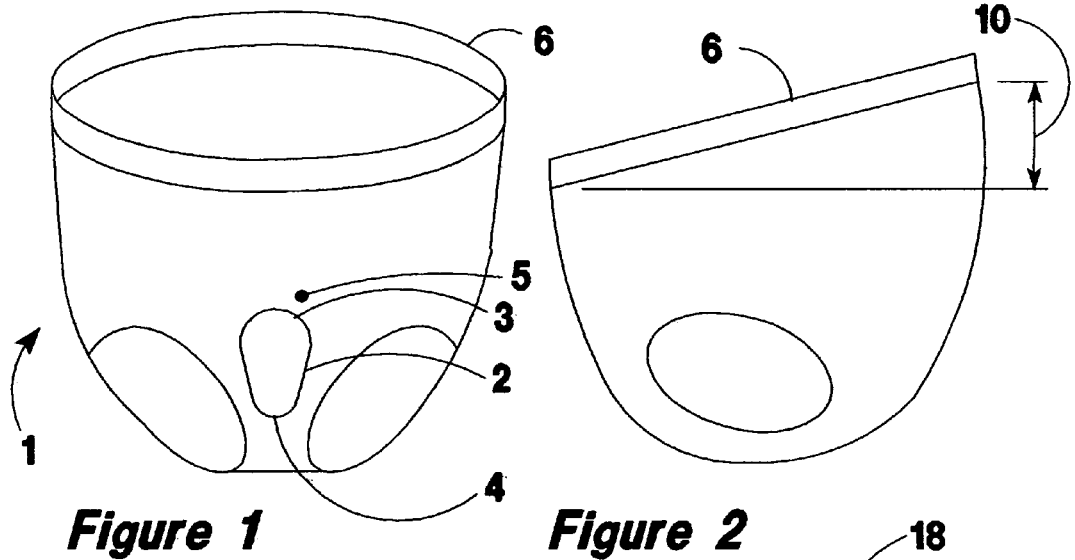
Figure 1  Figure 2
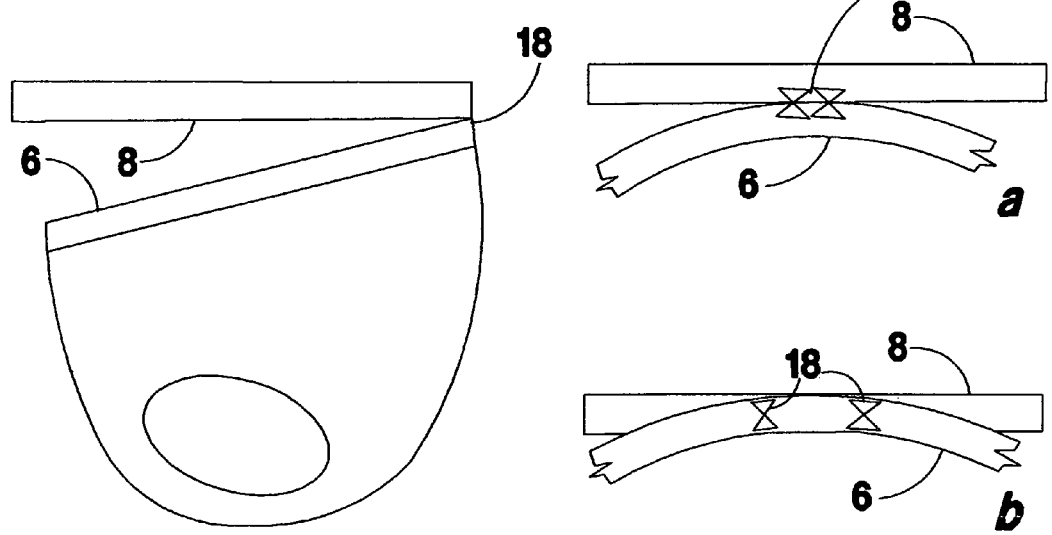
Figure 3  Figure 8

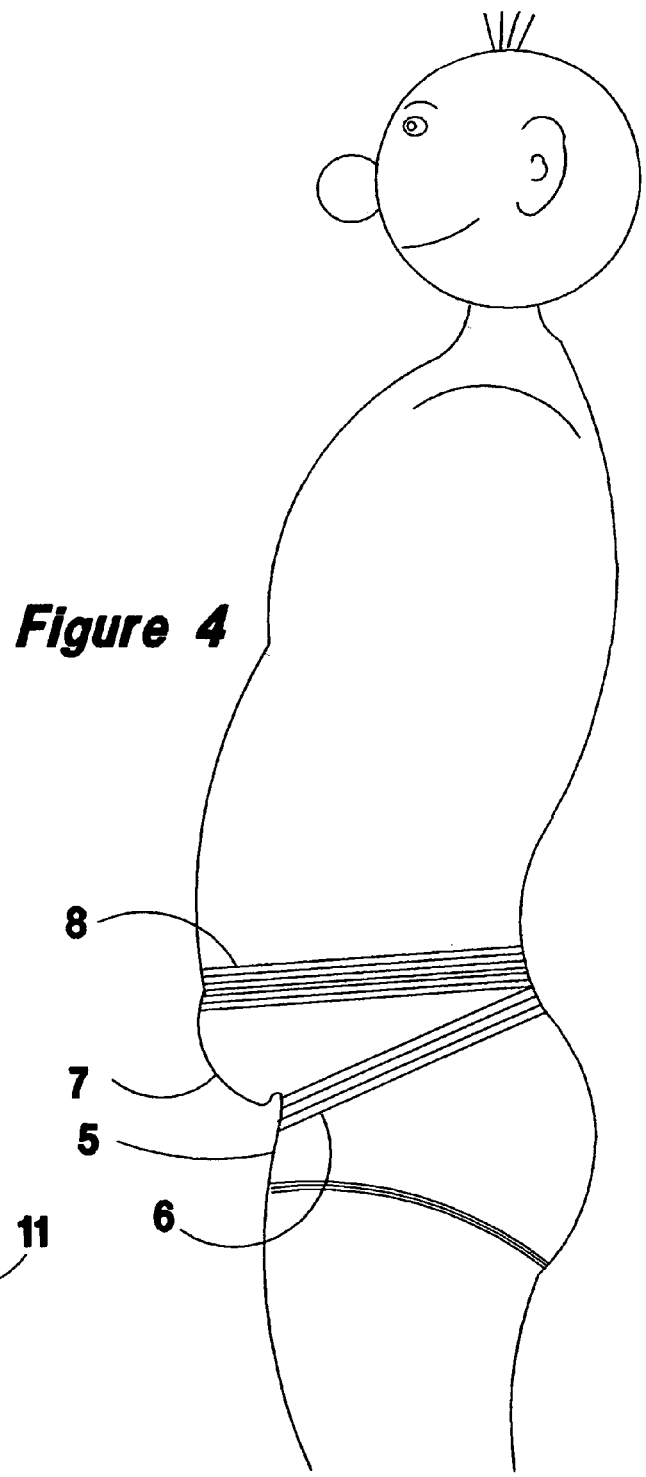
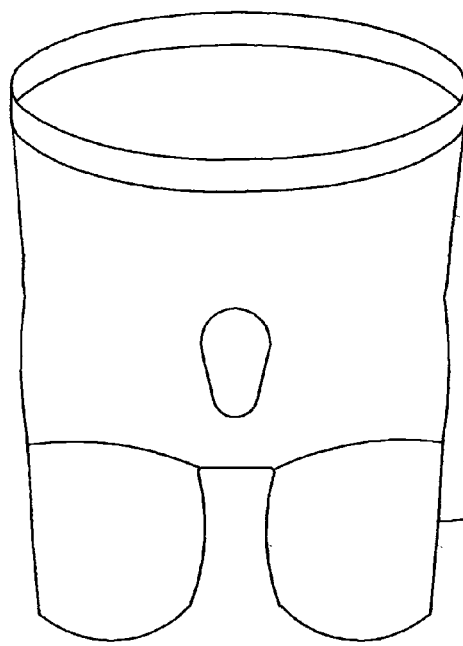
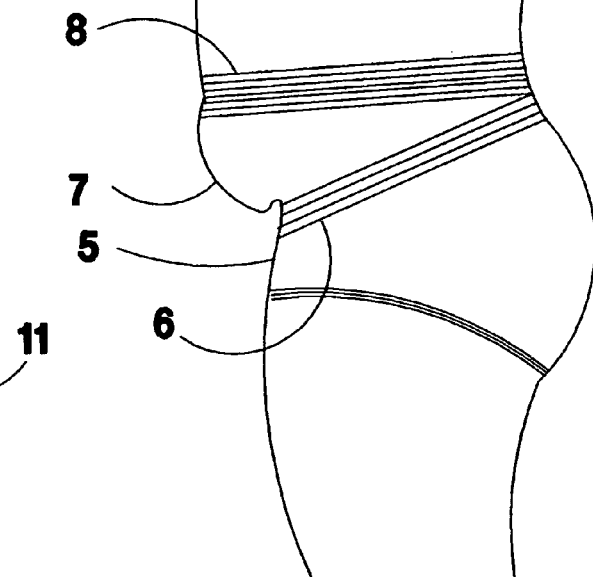

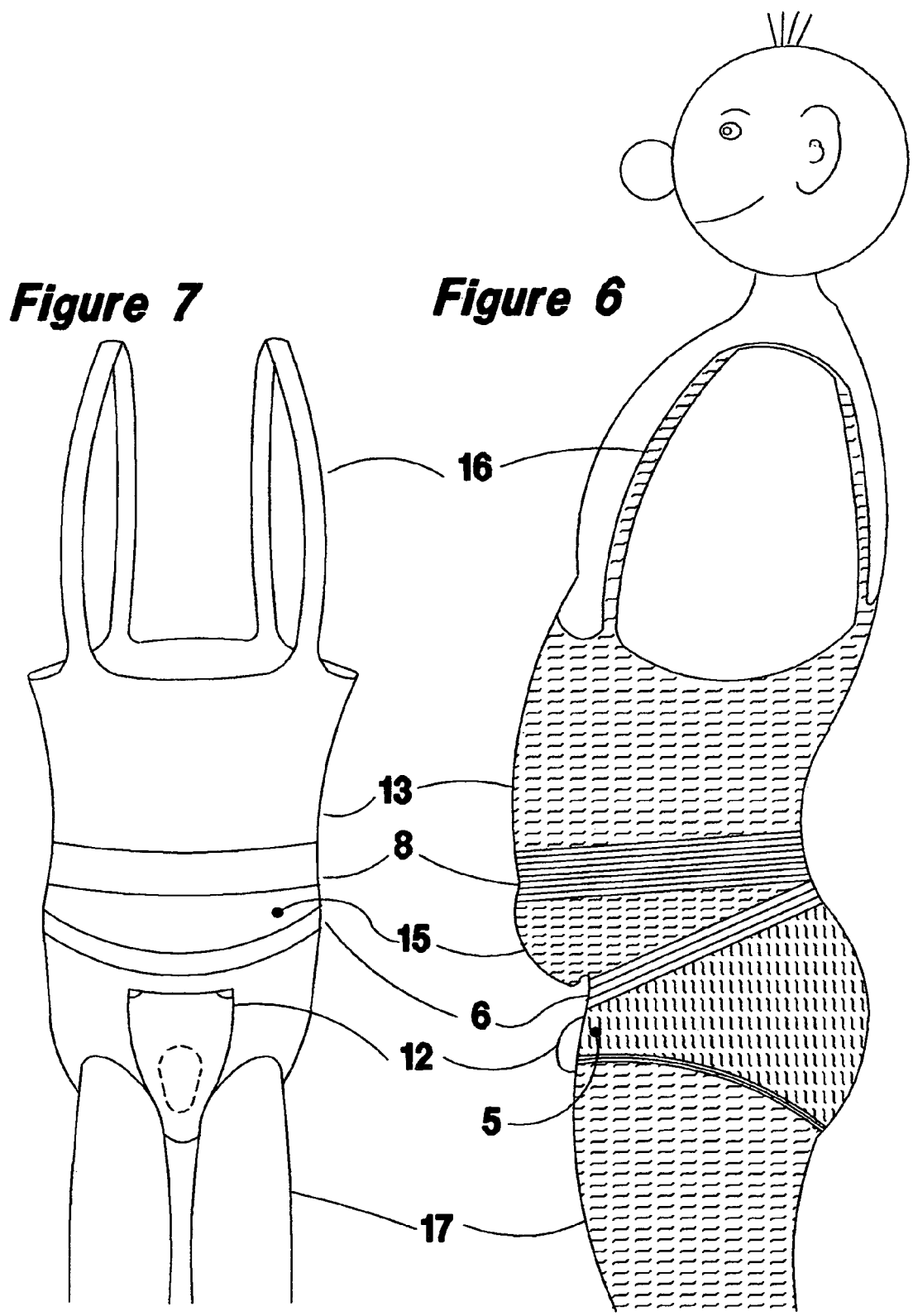

UNDERGARMENT FOR HERNIA RELIEF AND OTHER PURPOSES

RELATED APPLICATIONS

This application is a continuation of patent application Ser. No. 12/322,648 titled "Undergarment for Hernia Relief and Other Purposes" filed Feb. 5, 2009 (now abandoned) which is a continuation of application Ser. No. 11/147,693 titled "Garment for Enhancing Male Sexual Performance", filed Jun. 8, 2005, (now abandoned), which includes Provisional Application #60/580,115 titled "Garment for Enhancing Male Sexual Performance", filed Jun. 16, 2004. All three described applications are incorporated herein by reference.

U.S. GOVERNMENT INTEREST IN THE INVENTION

None

Definitions of Terms

Spandex: Spandex is the generic term for a polyurethane elastic filament. "Lycra" is Dupont's trade name for spandex filament. The term spandex is also applied to fabrics having elastic properties provided by spandex or similar elastic fiber. A review of textile manufactures, wholesalers, and swimsuit manufactures revealed that the spandex filament content of swimsuit fabrics ranges from 10 to 36 percent, with the most common being in the range of 15-20%.

This document intends that elastic fiber of other composition such as plastics, natural rubber, synthetic "rubber", etc, when woven into a fabric be included in the definition of "spandex fabric".

Two-Way and Four-Way Stretch Spandex Fabric:

The industry classifies spandex fabrics as either two-way or four-way stretch.

Four-way stretch fabric has elastic fiber in both the woof and warp axes, thus it has spandex fiber provided elasticity along two orthogonal axes. Two-way stretch fabric has elastic fiber in only one axis, thus exhibits spandex fiber provided elasticity along only one axis.

Elasticity: Elasticity, by common usage, and this disclosure, is imparted by actual elongation and restoration of fibers having rubber-like elastic properties. This is inherent in elastic fibers such as spandex fiber and rubber strands which, under tension, are capable of elongation and returning to original length when the tension is released. Some spandex may be lengthened as much as 500%. When knit or woven into a fabric, the fabric as a whole exhibits a rubber-like expand ability and contraction accompanied by noticeably significant force.

Some fabrics exhibit stretch ability by virtue of the weave having convolutions which are distorted under tension. Notable examples are knits such as in sweaters, and many knit cotton undergarments, in which the fabric may be readily distorted. The stretching and restoration is not accompanied by significantly strong forces in comparison to spandex containing fabrics. For the purposes of this document, these are not considered to be "elastic" fabrics. Thrower (U.S. Pat. No. 5,875,495) FIG. 9 illustrates a typical stretchable, but not elastic, fabric weave.

Sewing, Stitching:

Joining or attaching two or more fabric items by thread passing multiple times through the fabric pieces to be joined.

Panels:

The 5 zones of the garment, front (or pubic), back, left and right sides, and perineal coverings may be referred to as "panels".

"Panels" may refer to the zones, or to individual separate pieces of fabric which are to be, or are sewn together, or to portions of fabric pieces covering more than one zone.

Pot Belly, Pot:

An enlarged abdomen and may or may not include a hanging pouch of fat. Illustrated at FIGS. 4 and 6.

BACKGROUND OF THE INVENTION

1. Field of the Invention

Therapeutic garments and appliances.

2. Description of Related Art

U.S. Pat. No. 4,416,272 by Nedwyn Nelkin, teaches an hernia relief garment having some similarity to the present invention, however, it differs in important details. Nelkin has a brief type undergarment made of spandex and two belts as does the present invention. However the belts are not fastened to the brief in the same manner and place as the present invention, is not designed for, and will not fit a person with a "pot belly", as is the present invention. That is, the waistband (18) of the garment does not ride between the small of the back and low under the belly ("pot"). Thus, the Nelkin waistband (18) is likely to ride down under the belly and cause the front panel to loosen, bunch, lose its elastic properties, and purposes.

The Nelkin secondary band (4) is fastened to the garment at the front, not the back as is the present invention. Thus vertical adjustment is limited to the back of the band, whereas, in the present invention the belly band and waistband are attached together at the back and it is the front portion of the belly band that is vertically adjustable, as that is where abdominal hernias are likely to be present, not at the back.

U.S. Pat. No. 2,684,673 by Samuel Lerman is a intended for use as a binder or support for surgical dressings under the binder. There is no elasticity anywhere. However, there is a hole for admitting the wearer's penis and scrotum. The hole is pictured, but not described, as being an ovoid with the larger radius on the upper side. It is probable that the shape was not selected for function, but to generally conform to the tapering of the binder width in the vicinity of the hole.

U.S. Pat. No. 1,263,756 by Alfred Linneros, teaches a combination of a pair of non-elastic shorts (6) with a hole (10) and a connected undershirt (5).

The undershirt is buttoned at 4 points, not sewn, to the shorts. More specifically, the buttons (9) are carried on the shorts, and the cooperating button holes (8) are at the ends of shoulder straps (7) (lines 35-40). The phrasing at lines 35-36 and the dotted lines following the straps (7) over the shoulder in FIG. 1 suggest that the straps are sewn to the undershirt.

The buttoned shoulder straps are the only means to hold the shorts up; no draw string, no rubber bands (elastic bands), nor any other devices to keep them from slipping from the torso, and there is no specific waistband terminating the upper end of the shorts. A selvedged edge or hemmed edge are not deemed to be a waistband.

U.S. Pat. No. 5,875,495, by John H. Thrower, teaches an undergarment for men that has a hole for the receiving the penis and scrotum of the wearer.

Thrower's garment is intended primarily as an athletic supporter (col 2, lines 27-29 (2:27-29)). Thrower's hole is a symmetrical oval (figures and 4:2-5), not ovoid (egg shaped) as in the present invention. Thrower's garment, what he calls the "tubular body portion", is comprised of knit cotton. The only portion taught as comprising elastic fibers is the front covering (14) in some embodiments and the partial waist band (38) at the top of covering 14. The tubular portion is knit cotton which is stretchable due to the characteristics of the looping (knitting) of the fiber strands which permits the fabric to be stretched by distorting the knitted loops. The stretching force is minimal. The knitted cotton fabric panels have no spandex content.

Thrower does not teach that any of the knit cotton panels are elastic. Only front panel (14) is described as elastic. The knitted cotton portions are not considered as being elastic.

3. Objects of the Invention

It is an object of the invention to provide stabilization and relief for small hernias in the abdominal and perineal regions.

It is another object of the invention to provide adjustment of the positioning of the hernia stabilization means.

It is another object of the invention to be usable and effective for a wearer having an enlarged abdomen, a "pot belly".

It is another object of the invention to be a garment suitable as sleepwear.

BRIEF SUMMARY OF THE INVENTION

The present invention is comprised of four basic components which can be utilized in various combinations for use as an hernia support garment, as long-john type underwear, as athletic wear, and as sleepwear.

The four basic components are; a brief style spandex undergarment with the back cut higher than the front, an extra elastic band circling from the small of the back around the waist at near the navel in the front, a tank-type undershirt, and a pair of knit hose extending to the ankle. The undershirt is sewn to the elastic briefs to prevent creeping of the undershirt, the briefs, and the extra band. The extra elastic band, herein called the belly band, provides gentle pressure on small abdominal hernias thereby pressing them back into the peritoneal sack. The briefs are also optionally attached to a pair of hose having stirrups under the feet. The preferred material for both the undershirt and hose is knit material having stretch ability (deform ability), but little or no elasticity (force providing).

The elastic waist band of the briefs is differently placed compared to the band of ordinary under shorts. The back portion of the shorts is cut higher than the front, so the waist band is on a slope extending around the small of the back thence downward and under the abdomen of the wearer. The optional elastic belly band is attached to the waist band at the back and extends approximately horizontally around the midriff and over or near the navel.

The brief style shorts portion of the undergarment is constructed of either two-way or four-way stretch elastic fabric such as spandex ("Lycra™") or similar fabrics used in swimwear and athletic wear. The shorts component is constructed of spandex fabric all around. Thus pressures applied by the spandex hold small hernias of the groin in place to avoid strangulation of the intestines.

To avoid squashing the penis and testes, and to allow the front and perineum panels to snug against the body and provide more even pressures from the spandex fabric, especially in the perineum, the shorts are equipped with an egg-shaped hole through which the penis and scrotum are passed.

A BRIEF DESCRIPTION OF THE FIGURES

FIG. 1 illustrates the basic garment.
FIG. 2 illustrates the high-cut back of the present invention.
FIG. 3 illustrates the garment with the belly band added.
FIG. 4 illustrates the basic garment on a wearer showing the placement of the waist bands on a user.
FIG. 5 is an alternative embodiment of the basic garment having short legs.
FIG. 6 is a side view of an embodiment of the present invention with attached undershirt and hose.
FIG. 7 is a front view of an embodiment of the present invention with attached undershirt and hose.
FIG. 8 is a back side view of alternative joining of the elastic bands.

INDEX OF IDENTIFIED ELEMENTS

1. The invention.
2. The hole.
3. Upper arc.
4. Lower arc.
5. Elastic pubic covering panel (Front panel).
6. High-low positioning elastic waistband
7. Fat paunch.
8. The hernia belly band in place.
9. Not used.
10. Not used.
11. Leg part of an alternative embodiment of the present invention.
12. Front cover panel (modesty panel).
13. Tank top (undershirt) portion.
14. Not used.
15. Lower part of tank top.
16. Tank top shoulder strap.
17. Stocking (hosiery) portion.
18. Joining of the two elastic bands, stitching is illustrated, but any alternative means will suffice.

DETAILED DESCRIPTION OF THE INVENTION

The basic garment, ie, the brief portion, is illustrated by FIGS. 1 and 2.

The brief portion of the present invention is preferably constructed of elastic material such as is use in swim wear or athletic wear (10-36% spandex). The preferred fabric is four-way spandex of 15-20% spandex in all 5 panels, that is the front, back, left and right sides, and crotch panels. However, the crotch panel may be two-way spandex oriented front-to-back.

Generally, the brief is made by sewing the five panels together, but two or more of the panels may be fashioned from a single continuous piece of spandex comprising two or more panels. The description "panels" then refers to the position and function of sections of the single swatch of fabric.

Because there is no need for providing room for the male external organs, the pattern for cutting can be essentially the same as for women's swimwear with modifications to adapt to the male torso such as thicker waist, male abdominal shapes, etc. The pubic and perineal panels should fit snugly against the body. In conventional brief style underwear with the penis and scrotum being inside the garment, the crotch panel cannot stretch snugly over the perineum surface, nor can the pubic panel be snugged against the pubes.

An elastic waistband (6) is sewn to the top terminus of the torso surrounding panels, but unlike conventional briefs or even swimwear, the waistband is not worn essentially horizontal, but sloped downward from a high back fitted to pass over the small of the back and a low front passing under the abdomen. The primary function of the waistband is to anchor the briefs in one position, especially in the presence of an enlarged abdomen. The high back/low front cut places the brief's waistband in the natural position where there is no tendency to creep as is the case with ordinary straight across waistbands on conventional brief type underwear.

When the conventional brief type underwear waistband creeps down the front panel becomes loose and blouses. This is unacceptable in a spandex garment. It is essential for a spandex brief to keep the front panel flat and produce even pressure on the pubic area. While creeping and loosening is not a problem in conventional knit underwear, utilizing "precrept" waistband (6) like the present waistband would improve conventional style underwear.

Referring to FIGS. 2, 3, 4, and 7, the preferred characteristics of the waistband (6) is for it to be made in a continuous unbroken loop of two way spandex sewn all around, to the front, back, and side panels of the shorts. The dimensions are: 1 to 3 inches wide, and the back 2 to 5 inches higher (10) than the front so that the waistband fits into the small of the back and around the waist under the abdomen.

Alternatively the waistband may be formed by sewing a hem constructed of two or more layers the spandex panels folded over.

The high-low waistband will function in exactly the same manner when worn by a thin man.

Another advantage of the high back/under-the-abdomen waist band is that the position shown in FIG. 4 is a smaller circumference than the ordinary more horizontal position approximately in the position of the belly band (8). In fact the high/low position is the smallest circumference of any waist measurement of a portly person. This means that an elastic in position of (6) will have less hoop tension than other positions of wearing, and that the propensity of an elastic waist band or belt to slip down is greatly reduced as it is already "slipped down".

The preferred penis/scrotum hole (2) is a vertically oriented ovoid (egg) shape with the upper arc (3) having a radius of approximately ¾ inch and the lower arc 4 having a radius of approximately ½ inch. The vertical length of the preferred hole is approximately 2½ to 3½ inches with the variation being at the lower end of the hole. Like any garment, the positioning and the specific size of the hole and other garment parts is fitted to match the body size of the wearer. In no case should the hole be so small or misplaced as to pinch the sides or top of the penis, or to bind at the underside of the scrotum. A front covering (12) is optional, but valued when the garment is used as a hernia brace or as general underwear. The covering 12 is made of knit cotton or any other material and weave suitable for the application. It is fastened to or near the lower edge of the waist band (6) and to the perineal (crotch) panel. Covering (12) is loose enough to form a pocket for the organs without significant binding. The fastening may be by any convenient method such as, tack sewing, buttons, snaps, ties, Velcro, etc, and may include attachment along the sides of cover panel (12).

Other purposes for the cover panel (12) are for modesty, to prevent abrasion, for hygiene, and for comfort.

The second hernia relief element of the invention is an optional elastic belly band (8) 2 to 4 inches wide. The belly band is spot sewn to the briefs portion of the invention basic garment waist band (6) at the back by either of the methods shown in FIG. 8. FIG. 8a illustrates preferred method of joining the belly band (8) to the waistband (6) being sewn edge to edge. A small overlap to facilitate machine stitching is deemed to be edge-to-edge. This preferred attachment allows the belly band (8) to pivot at the back while the front is adjusted up and down.

FIG. 8b illustrates the bands being heavily overlapped and sewn together in the overlapping zone. This configuration has less pivot ability than the embodiment shown in FIG. 8a, and may introduce unbalanced elastic forces tending to cause the belly band to slip down away from its set position.

The elastic belly band (8) is generally placed over or near the navel and is adjusted to cover, flatten, and hold abdominal hernias.

Pads may be inserted as needed under the front or side pressure panels, waistband, or the belly band.

Referring to FIGS. 6 and 7, the third part of the invention is the addition of a shirt portion in the general form of an undershirt.

The undershirt portion (13) of the garment is of cotton knit or other suitable materials and weaves. The shoulder straps (16) convey additional lift to the waist bands and lower abdominal portion, especially if there is a hanging pouch of fat. Some spandex may be included in some locations for a conforming fit and support. The undershirt portion is sewn to the elastic waistband (6) at least at the front half, and preferably all around. The belly band (8) is left unattached to the undershirt to be free for adjusting up or down. Among other things, the attached undershirt prevents the waistband from folding, which would result in pinching and binding. Obviously, the undershirt's attachment to the brief portion also prevents the undershirt from creeping upward on the torso.

Upper band (8) is omitted in some embodiments. The undershirt is cut lower under the arms than most tank-top undershirts to give additional length to the shoulder straps so they may be more easily pulled over the shoulders. The top of the torso portion under the arms should end approximately 14 to 16 inches below the top of the shoulder. The front and back undershirt panels may be extended higher than shown in FIGS. 6 and 7.

Referring again to FIGS. 6 and 7, the fourth part of the invention is the addition of a legging or hose portion in the general form of an long-john type legwear sewn to the leg openings of the brief portion, and extending to the ankle, terminating in stirrup straps passing under the insteps of the feet.

The purpose of the hose portion is primarily for warmth when used as an undergarment in cold weather and as sleepwear.

How to Use the Invention:

The garment is pulled on over the buttocks and pelvis, and the penis and scrotum is pulled through the hole, and the belly band (8), if used, is adjusted to cover any abdominal hernias.

Alternative Embodiments and Usages

The brief design (described as the basic garment) shown in FIG. 1 can be modified by adding short legs (11) as shown in FIG. 5 for both the preferred usage, and the comfort-sleep wear described below.

The garment can be modified for enhancing comfort while sleeping, and in particular will provide a cooling effect on the testes during hot, humid nights, although the comfort feature is useful even on cool nights. For sleepwear and athletic wear, slight modifications of the described invention is desired. The modifications are to have short legs (11) as shown in FIG. 5, and a covering panel made of cotton or similar absorbent fabric. This embodiment puts a layer of cloth between the penis and scrotum and the leg during sleeping. Thereby reducing sweating and absorbing whatever sweat does occur at the contact area. The fabric not only controls sweating, but because of the contact area being dryer, the growth of fungus and bacteria is inhibited or eliminated. The cooling effect should also be healthier for the testes, which are sensitive to heat.

I claim:

1. A garment for compressing extended hernias comprising:
   a. a brief style under garment having cooperatively inter-connected spandex elastic panels adapted or cover the pubic, hip sides, perineal, and buttock areas of a wearer, said inter-connected panels comprising a circular top edge having an elastic waistband sewn thereon, said waistband being adapted to encircle the wearer's torso passing over the small of the wearer's back thence downward and passing under the wearer's abdomen; and
   b. an ovoid shaped hole in the pubic panel adapted for receiving a penis and scrotum of the wearer, wherein said ovoid hole having a long axis and a short axis, wherein said long axis is vertically oriented, said ovoid hole having an upper and lower arc edges, wherein said upper arc edge having a larger radius than said lower arc edge; and
   c. where said elastic panels, elastic waistband, and hole cooperate to apply strongly palpable pressure to the pubic and perineal surfaces, and no pressure to the penis or scrotum of the wearer; and
   d. further comprising a second elastic band adapted to put pressure on, and hold, abdominal hernias, said second elastic band being of sufficient width to cover an abdominal hernia, said second elastic band is positioned directly above the waistband and is sewn to said waistband at the back only, whereby the front and side portions of said second elastic band may be moved up or down over an abdominal hernia.

2. The garment of claim 1 further comprising an undershirt having shoulder straps, and a torso surrounding portion having a lower edge, said lower edge sewn to said waistband, said sewing being continuous along the entire top edge of said waistband.

3. A garment for compressing extended hernias comprising:
   a. a close fitting brief style garment adapted to be worn by an human male, said garment having cooperatively inter-connected spandex elastic panels configured for covering the pubic, hip sides, perineal, and buttock areas of a wearer, and an elastic waistband sewn to said inter-connected panels, said waistband being adapted to encircle the wearer's torso passing over the small of the wearer's back thence downward and passing under the wearer's abdomen; and
   b. said elastic panels extending upward to said waistband wherein said waistband is a continuous unbroken loop sewn to the upper edges of said elastic panels; and
   c. an ovoid shaped hole in the pubic panel adapted for receiving the penis and scrotum of the wearer; and
   d. said ovoid shaped hole being vertically oriented with the arc of the upper end being larger than the arc of the opposite lower end, and the lower arc being oriented downward toward the perineal panel; and
   e. where said elastic panels, elastic waistband, and hole cooperate to apply strongly palpable pressure to the pubic and perineal surfaces, and no pressure to the penis or scrotum of the wearer;
   f. further comprising a second elastic band adapted to put pressure on, and hold, abdominal hernias, said second elastic band being of sufficient width to cover an abdominal hernia, said second elastic band is positioned directly above the waistband and is pivotally attached by being sewn to said waistband at the back only, whereby the front and side portions of said second elastic band may be moved up or down over an abdominal hernia; and
   h. the garment further comprising an undershirt having shoulder straps, and a torso surrounding portion having a lower edge, said lower edge sewn to said waistband, said sewing being continuous along the entire top edge of said waistband.

* * * * *